United States Patent [19]

Shoesmith

[11] Plant 4,328

[45] Oct. 31, 1978

[54] CHRYSANTHEMUM NAMED BUCKEYE

[75] Inventor: Leonard H. Shoesmith, Westfield-Woking, England

[73] Assignee: Pan-American Plant Company, West Chicago, Ill.

[21] Appl. No.: 798,088

[22] Filed: May 17, 1977

[51] Int. Cl.[2] ..... A01H 5/00

[52] U.S. Cl. ..... Plt./74

[58] Field of Search ..... Plt./74–75

*Primary Examiner*—Robert E. Bagwill

*Attorney, Agent, or Firm*—Chas. W. Rummler

[57] ABSTRACT

A new and distinct chrysanthemum cultivar adaptable to both year around greenhouse pot culture and as a natural season flowering garden plant, characterized by its relatively large blooms of single flower form and unique coloring with dark red ray florets and yellow-orange disc florets, the flowers being displayed in a relatively open spray formation. As a pot plant, this cultivar has an excellent performance for spring, summer and fall 4 to 5 inch pot culture with a uniform 7-week flowering response to photoperiodic control, and it has a relatively vigorous plant habit with average stem strength and medium sized foliage.

3 Drawing Figures

BACKGROUND OF THE NEW PLANT

This chrysanthemum plant originated in 1972 as a seedling of unidentified parentage and was discovered by me among some random pollinated plants growing in my breeding grounds at Westfield-Woking, Surrey, England. Its unique coloring prompted me to reproduce the plant by means of cuttings from the original plant to test its possibilities for commercial exploitation and subsequent propagation of the plant by vegetative cuttings at Westfield-Woking, Surrey, England, and at West Chicago, Ill., has shown that its distinctive features hold true from generation to generation and appear to be firmly fixed.

DESCRIPTION OF THE DRAWINGS

My new chrysanthemum cultivar is illustrated by the two accompanying drawings, one of which is a photographic print in full color showing a potted plant of this variety in full bloom and the other of which is a print of a mechanical photocopy of typical leaves of the new plant taken at various stages of maturity. The colors of the photographic drawing are as nearly true as it is reasonably possible to obtain by conventional photographic procedures, the photograph being of a plant grown at West Chicago, Ill., and flowered in February 1977.

DESCRIPTION OF THE NEW PLANT

The following is a detailed description of my new chrysanthemum cultivar with color designations according to the R.H.S. Colour Chart published by The Royal Horticultural Society of London, England, the observations stated having been made of plants grown in greenhouse at West Chicago, Ill.

THE PLANT

Origin: Seedling.

Parentage: Unidentified, the plant having been found among random pollinated plants of similar varieties.

Classification:

*Botanic.*—*Chrysanthemum Morifolium.*

*Commercial.*—Greenhouse pot plant and outdoor garden chrysanthemum.

Form: Perennial herbaceous bush.

Height: 5 to 8 inches as a pot plant. 15 to 21 inches as an outdoor garden plant.

Growth: Terminal, vigorous and upright with stem strength and sturdiness, but with a tendency to weakness at the soil line.

Foliage: Quantity — abundant with six to eight leaves per 4 inches of stem.

*Leaf size.*—Length — 1⅝ to 4 inches. Width — 1 to 2⅜ inches. Shape: Lanceolate, lobed and deeply serrated. Color: Upper side — Yellow-Green 147A. Under side — Yellow-Green 147B. Surface texture: Canescent. Venation: Pinnately veined.

*Petioles.*—About 5/16 to ¾ inch long.

THE BUD

Form: Globular.

Size:

*Diameter.*—3/16 to 5/16 inch.

*Depth.*—About ¼ inch.

Opening: The bud opens slowly.

Color:

*When phyllaries first divide.*—Greyed Red 180C and Yellow-Green 144A.

*When florets begin to unfurl.*—Greyed Red 181A and Greyed Purple 184A.

Phyllaries: Many in number, borne as involucral bracts on the outside of the receptacle.

*Form.*—Spear-shaped.

*Color.*—Inside — Yellow-Green 146C. Outside — Yellow-Green 147B.

*Surface texture.*—Pubescent.

*Peduncle.*—Length — About ½ to ⅞ inch. Surface texture: Pubescent. Strength: Erect and strong. Color: Yellow-Green 148C.

THE FLOWER

Blooming habit: This plant can be flowered the year around with photoperiod control.

*Response.*—7 weeks.

*Recommended flowering.*—March 1 to November 1.

*Natural season flowering.*—About September 26 to October 9.

Blooms:

*Flower type.*—Composite and single.

*Size of bloom.*—Large. Diameter: 1⅛ to 3 inches. Depth: 9/16 to 1 inch.

*Shape.*—Cup-shaped. The shape does not change as flower matures.

*Borne.*—Singly, as a head of many florets carried by a receptacle in an open spray formation.

*Florets.*—Quantity — Numerous. Form: Single and generally linear with obtuse to acute apex. Arrangement: three to four rows of ray florets, generally imbricated. Texture: Medium firm. Appearance: Very slight shine. Discoloration: Moderate fading.

*Color.*—The following colors were observed in March 1978 on flowers of a greenhouse plant of this variety. Outer Florets: Upper side — 46A and B; 53A and B; 45 A. Under side — 182C and D; 51B and C; 179B. Disc Florets: Center — 17A. Perimeter — 17A.

*General color tonality.*—46A-46B when viewed from a distance of 6 feet.

Effect of weather: This plant is not affected by hot or wet weather.

Persistence: The florets hang on and dry.

Fragrance: Typical chrysanthemum.

Lasting quality:

*On plant.*—3 weeks.

*As cut flower.*—Not recommended.

REPRODUCTIVE ORGANS

Stamens:

*Number.*—5.

*Arrangement.*—Syngenesious.

*Filaments.*—About 1/16 to ⅛ inch long. Color: Light Yellow.

*Pollen.*—Color — Yellow.

Pistils: Number — One to each disc and ray floret.

*Styles.*—About ⅛ to 3/16 inch long.

*Stigmas.*—Color — Yellow.

Ovaries: Inferior bicarpellate.

This new chrysanthemum plant is distinguished by its single flower form with dark red ray florets extending from a disc of yellow florets, the large size of its blooms borne in a relatively open spray formation, and its moderate production of pollen. As a greenhouse plant, this new variety has a uniform 7-week flowering response, excellent performance as a spring, summer and fall 4 to 5 inch potted plant. The plant has a relatively vigorous and upright growth habit and excellent performance as a natural season garden chrysanthemum, and when grown as a potted plant may require some growth retardant treatment. It has average stem strength with a tendency to be weak at the soil line and a susceptibility to high soluble salt conditions.

I claim:

1. The new and distinct chrysanthemum cultivar substantially as herein shown and described, characterized by its large sized blooms of single flower form with dark red ray florets and yellow disc florets, by its excellent performance as a natural season garden chrysanthemum and as a spring, summer and fall potted plant, and by its uniform 7-week photoperiodic flowering response for greenhouse pot plant culture.

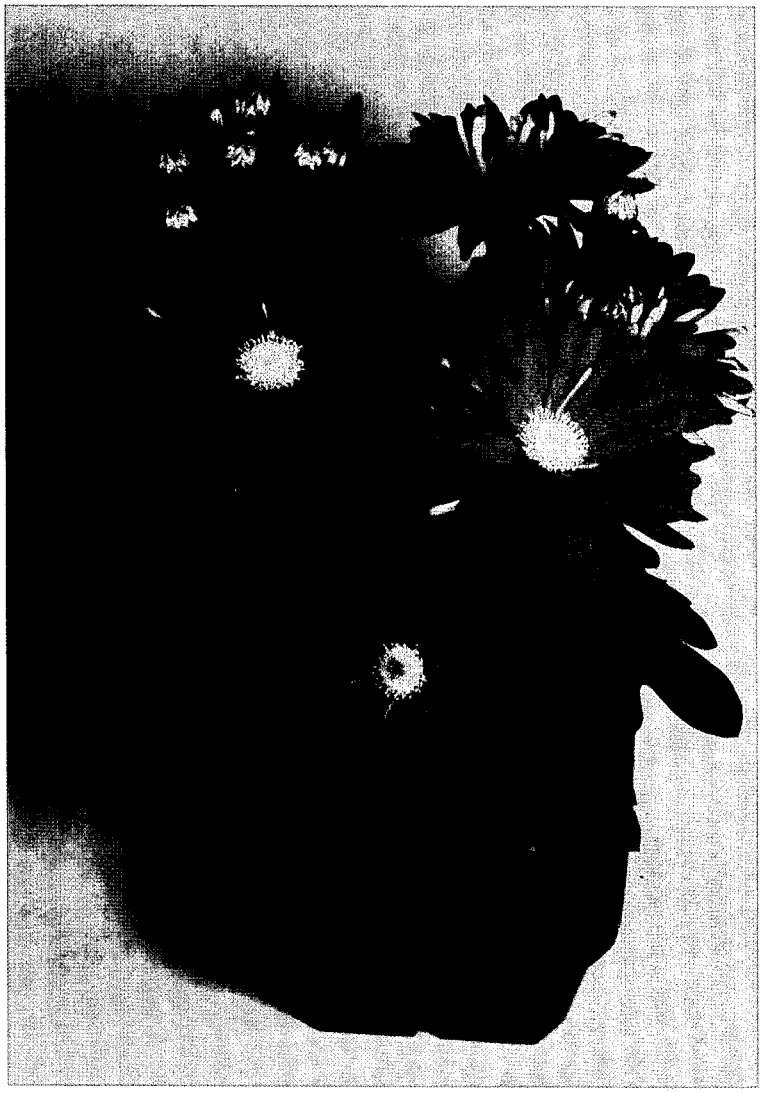

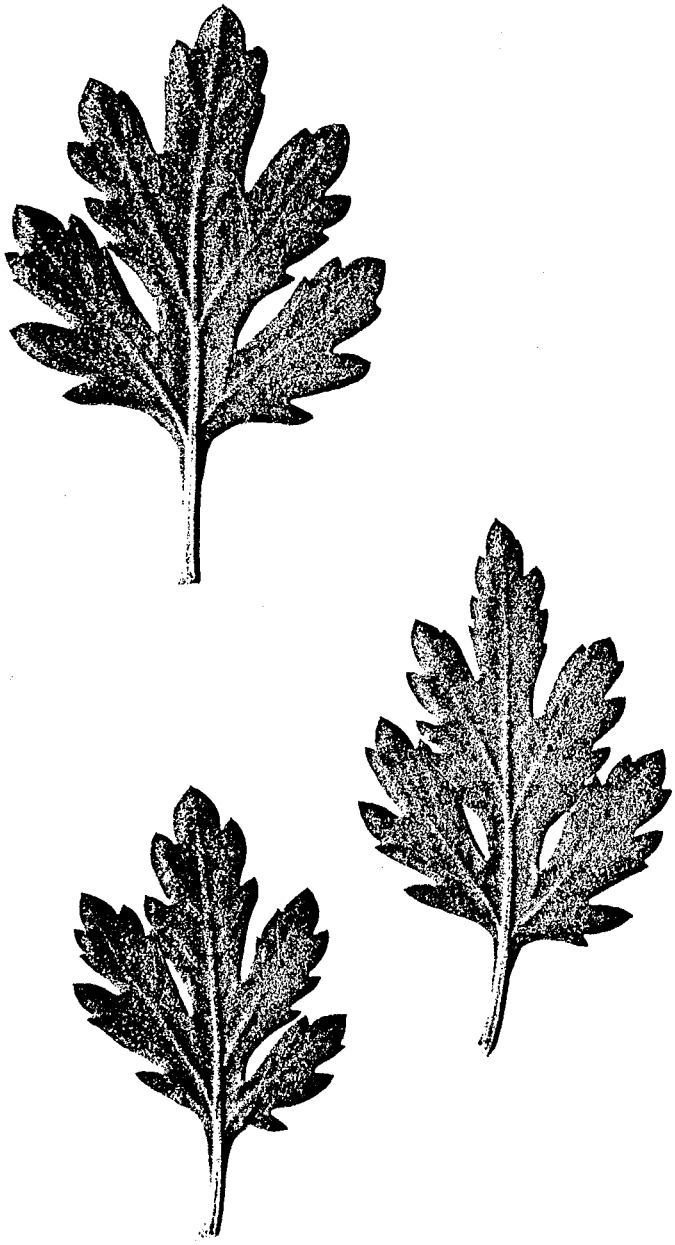

* * * * *